United States Patent
Hodge

(10) Patent No.: US 9,316,624 B2
(45) Date of Patent: Apr. 19, 2016

(54) SYSTEM AND METHOD FOR VARIABLE SPEED FEEDBACK CONTROL CHROMATOGRAPHY LOADING

(75) Inventor: Geoffrey L. Hodge, Sutton, MA (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 488 days.

(21) Appl. No.: 13/277,888

(22) Filed: Oct. 20, 2011

(65) Prior Publication Data

US 2012/0118828 A1    May 17, 2012

Related U.S. Application Data

(63) Continuation-in-part of application No. PCT/US2010/032164, filed on Apr. 23, 2010.

(60) Provisional application No. 61/172,030, filed on Apr. 23, 2009.

(51) Int. Cl.
| | |
|---|---|
| *G01N 30/32* | (2006.01) |
| *G01N 30/86* | (2006.01) |
| G01N 30/74 | (2006.01) |
| G01N 30/46 | (2006.01) |

(52) U.S. Cl.
CPC ............ *G01N 30/32* (2013.01); *G01N 30/8658* (2013.01); *G01N 30/461* (2013.01); *G01N 30/74* (2013.01); *G01N 2030/324* (2013.01); *G01N 2030/326* (2013.01)

(58) Field of Classification Search
CPC .............. G01N 30/32; G01N 30/8658; G01N 2030/326; G01N 2030/324; G01N 30/461; G01N 30/74

USPC .......... 210/656, 659, 101, 143, 198.2; 422/70
See application file for complete search history.

(56) References Cited

U.S. PATENT DOCUMENTS

| | | | | |
|---|---|---|---|---|
| 3,923,460 | A * | 12/1975 | Parrott et al. ................. | 436/149 |
| 3,981,801 | A * | 9/1976 | Knox ............................. | 210/656 |
| 4,028,056 | A * | 6/1977 | Snyder et al. ................. | 436/514 |
| RE29,454 | E * | 10/1977 | Ashmead et al. ................ | 222/1 |
| 4,478,713 | A * | 10/1984 | Girot et al. .................... | 210/101 |
| 4,599,115 | A * | 7/1986 | Ando et al. .................. | 127/46.1 |
| 4,724,081 | A * | 2/1988 | Kawahara et al. ............ | 210/659 |

(Continued)

FOREIGN PATENT DOCUMENTS

| | | |
|---|---|---|
| EP | 1 544 612 | 6/2005 |
| EP | 1 879 026 | 1/2008 |

(Continued)

OTHER PUBLICATIONS

Extended European Search Report dated Nov. 4, 2013 issued on corresponding EP application No. 10767812.0.

*Primary Examiner* — Ernest G Therkorn
(74) *Attorney, Agent, or Firm* — Grogan, Tuccillo & Vanderleeden, LLP

(57) ABSTRACT

Disclosed herein is a chromatography system wherein a sensor, for example, a UV sensor, is tied to a continuously variable load pump in a feedback control loop, with an option to divert the feed stream back to the load vessel or reservoir or onto a second chromatography column, the disclosed chromatography system allowing a true feedback control across variable load rates, thereby adjusting chromatographic operating parameters, for example, variable load rates, to process conditions, while maximizing throughput.

5 Claims, 2 Drawing Sheets

(56) References Cited

U.S. PATENT DOCUMENTS

| | | | |
|---|---|---|---|
| 4,772,388 A | | 9/1988 | Allington |
| 4,840,730 A | * | 6/1989 | Saxena .................... 210/198.2 |
| 5,102,553 A | * | 4/1992 | Kearney et al. ............ 210/659 |
| 5,360,320 A | * | 11/1994 | Jameson et al. .............. 417/4 |
| 5,630,943 A | * | 5/1997 | Grill .......................... 210/659 |
| 5,670,054 A | * | 9/1997 | Kibbey et al. .............. 210/656 |
| 7,186,336 B2 | * | 3/2007 | Gerhardt et al. .......... 210/198.2 |
| 2005/0121392 A1 | * | 6/2005 | Hoffman .................... 210/656 |
| 2008/0116122 A1 | * | 5/2008 | Wheelwright et al. ....... 210/87 |
| 2009/0294363 A1 | * | 12/2009 | Liu .............................. 210/656 |

FOREIGN PATENT DOCUMENTS

| | | |
|---|---|---|
| WO | WO 01/88528 | 11/2001 |
| WO | WO 02/068954 | 9/2002 |

* cited by examiner

SYSTEM AND METHOD FOR VARIABLE SPEED FEEDBACK CONTROL CHROMATOGRAPHY LOADING

RELATED APPLICATIONS

This application is a Continuation-in-Part of International Application PCT/US2010/032164, which designated the United States and was filed on 23 Apr. 2010, published in the English language, and which claims the benefit of U.S. Provisional Application No. 61/172,030, filed on 23 Apr. 2009. The entire teachings of the above applications are incorporated herein by reference.

BACKGROUND

In the process of chromatography, a mixture of chemical substances may be resolved or separated by means of their selective retardation as they are transported by a moving fluid or buffer solution through a resin packed in a chromatography column. A solution of the substances to be separated is referred to as the mobile phase of the system. The resin is known as the stationary phase and comprises finely divided particles which may be in the form of a gel slurry.

A chromatography column, referred to herein as simply a "column," typically comprises a hollow, vertically disposed cylindrical housing including, at the upper end, a liquid dispensing section through which the mobile phase is dispensed to the porous resin. A liquid collecting section is located at the lower end of the column. The resin through which the mobile phase percolates is located between these sections.

The mobile phase is pumped or poured into the top of a chromatography column filled with the resin to which the substances to be separated can bind differentially as the mobile phase percolates down the column.

Binding of chromatography resins is known to generally increase with increasing residence time, that is, contact time with the resin in the chromatography column. In the field of bio-manufacturing, there has been a well-recognized need to choose between the loading of columns at relatively fast flow rates in order to complete steps quickly, versus the loading at a slower flow rate in order to maximize resin binding, the slower flow rate resulting in an increase in process time. Traditionally an acceptable middle ground has been chosen as a compromise option. At a given flow rate, as binding sites on the resin become occupied, resin capacity decreases because the percentage of available binding sites decreases with increased time.

Experiments relating to dual flow rate loading have been described, wherein material is loaded quickly at first; then loaded at a lower flow rate once the resin capacity is decreased. Additionally, techniques such as simulated moving bed (SMB), and simultaneous multi-column chromatography (SMCC) have been developed. These techniques seek to make better use of the resin over time by dividing the resin volume over multiple columns, each of which can be operating in a different portion of the chromatography sequence, for example, equilibration; load; wash; elution; and strip.

In the field of bio-manufacturing, recent developments in techniques of cell culture have increased productivity. However, the productivity and economics of bio-manufacturing are still limited by downstream processing, especially by the widely used technique of bind-and-elute chromatography.

Thus, a need exists for a new system for adjusting chromatographic operating parameters to process conditions, while maximizing throughput, the operating parameters including, for example, variable load rates.

BRIEF SUMMARY OF THE DISCLOSURE

The inventor of the present subject matter has now discovered an improved system and method of chromatography, including a variable speed feedback control chromatography loading process and device that can increase the efficiency of chromatography such that downstream purification can be accomplished at an increased rate. This improvement in chromatography efficiency, together with current increases in cell culture productivity can speed the production of vaccines and therapeutic molecules.

Disclosed herein is a chromatography system for monitoring a process condition and in real time adjusting a chromatographic operating parameter to the process condition, the chromatography system comprising: a first chromatography column having an inlet end and an outlet end and adapted to contain a porous matrix; a pump having a continuously variable pumping speed and arranged to pump a fluid at a continuously variable rate from a reservoir into the inlet end of the chromatography column; a main downstream effluent path extending from the outlet end of the chromatography column, the main downstream effluent path for generally directing an effluent flowing out of the outlet end of the chromatography column; a closeable bifurcated fluid path communicatively coupled to the main downstream effluent path, the closeable bifurcated fluid path including: a first flow path for directing at least a first portion of the effluent back to the reservoir; and a second flow path for directing at least a second portion of the effluent to an exit of the chromatography system or to a second chromatography column; a sensor positioned in the main downstream effluent path and configured to detect at least one signal indicative of the presence or absence of a component in the effluent, wherein the component is indicative of a process condition within the chromatography system; a controller operably connected to the sensor, and to the pump; a first valve operably connected to the controller and positioned in the first flow path such that when the first valve is in an open position, effluent can flow back to the reservoir or to a second chromatography column; and a second valve operably connected to the controller and positioned in the second flow path, such that when the second valve is in an open position, effluent can exit the chromatography system, and wherein the position of the first valve and the position of the second valve are each operably controlled by the controller.

In another embodiment, the invention relates to a method of monitoring a process condition within a chromatography system and adjusting in real time a chromatographic operating parameter to the process condition, the method comprising:

obtaining a chromatography system as described in the preceding paragraph;

pumping the fluid at a continuously variable rate from the reservoir into the inlet end of the first chromatography column;

allowing the fluid to flow through the porous matrix contained within the first chromatography column and to form an effluent flowing out of the outlet end of the first chromatography column and into the main downstream effluent path;

allowing the sensor positioned in the main downstream effluent path to detect a signal indicative of the presence of a component in the effluent, wherein the component is indicative of a process condition within the chromatography system;

allowing the sensor to send a signal to the controller, the signal indicating the presence or absence of a component in the effluent;

allowing the controller to analyze the signal from the sensor to determine the presence or absence of the component in the effluent;

allowing the controller, in response to the analysis of the signal, to slow the rate of pumping of the fluid in order to increase residence time of the component at the porous matrix, or to increase the rate of pumping of the fluid;

and to signal adjusting the first valve and/or the second valve in order to at least partially open or close the first valve and/or the second valve, thereby monitoring a process condition within the chromatography system and adjusting in real time a chromatographic operating parameter to the process condition.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
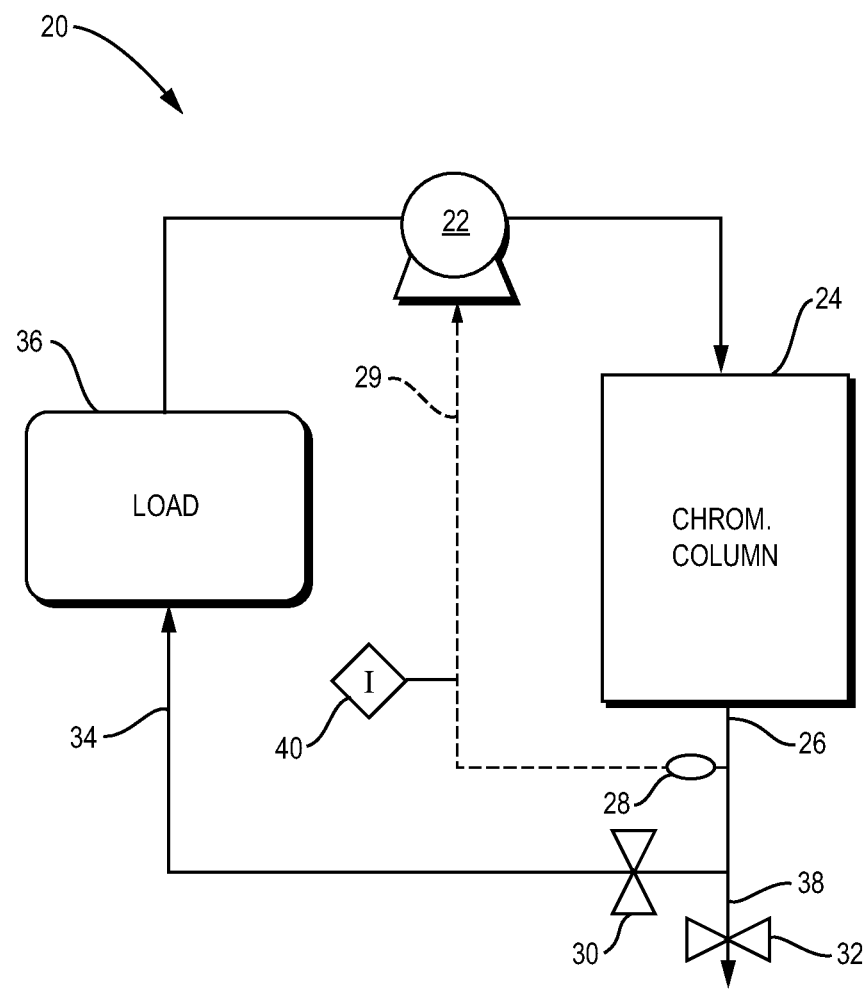
FIG. 1 is a schematic representation of one embodiment of a system for variable speed feedback control chromatography loading.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The disclosed system makes use of some standard chromatography components. Generally stated these are a: 1) a means of pushing liquid through the system, 2) a means of separation of molecules based on some physical or chemical property, 3) a means of detection, monitoring, and measurement of the post-separation stream.

In one embodiment of the invention a system includes a continuously variable speed load pump or other suitable means for pushing liquid through a chromatography column; a chromatography column adapted to contain a porous matrix, such as a resin, or a membrane adsorber; and a detector or sensor such as, for example, a UV detector. Other non-limiting examples of a sensor suitable for use in an embodiment of the invention are a conductivity sensor, a pH sensor, a dissolved gas sensor, and a turbidity sensor. The sensor used in the disclosed invention may be single use or disposable; or it may be re-useable. The chromatography column can be of any type, including a monolith column. The chromatography column may be single use or disposable; or the column may be re-useable. In one embodiment of the invention, all or a portion of the disclosed system is re-useable. In another embodiment, all or a portion of the disclosed system is single use or disposable.

Traditionally a pump utilized in a prior art chromatography system is operated at a single speed, or by decreasing the speed part way through the loading process. It has now been discovered that continuously varying the speed of the pump to vary the flow rate in response to continuous signals detected by the sensor, signals indicative, for example of a concentration of product or contaminant present in the effluent, greatly increases the efficiency of a chromatography process. The innovation disclosed herein comprises both a process innovation and a corresponding equipment innovation, wherein the detector, that is, the sensor, is used to continuously control the speed of the continuously variable speed pump.

According to an embodiment of the invention, the sensor can detect a signal in a main downstream effluent path, for example, the signal indicative of the presence or absence of a component in the effluent, and wherein the component is indicative of a process condition within the chromatography system. For example, as the column capacity is nearing saturation, the concentration of a product or a contaminant of interest in the effluent increases over time and is monitored and detected by the sensor. The sensor is in a feedback control loop with the pump and a controller which controls the speed of the pump, thereby varying the speed of loading of a fluid on the column. The load rate can be relatively high when the column is fresh. As column capacity decreases with time, the product or contaminant will be bound at a lower rate. "Breakthrough" is said to occur when the product or contaminant appears in the column effluent and is detected by the sensor. In response to a signal from the sensor, the controller can slow the pump, thereby slowing the flow rate and slowing the loading of the column.

Turning now to FIG. 1, which is a schematic representation of one embodiment of a system 20 for variable speed feedback control chromatography loading, the pump 22 is arranged for pumping a fluid or load from reservoir 36 into chromatography column 24 at variable flow rates, which flow rates may be continuously or infinitely variable.

Pump 22 may be operably connected to a first driver circuit in the computer, also referred to herein as a microprocessor or programmable logic controller (PLC), hereinafter, the "controller 40."

In one embodiment of the invention, at least one sensor 28 positioned in the main downstream effluent path 26, a flow path downstream of the bottom drain aperture (not shown) of column 24, can be operably connected to a second driver circuit in the controller 40.

In one embodiment of the invention, a closeable bifurcated fluid path is communicatively coupled to the main downstream effluent path 26, the closeable bifurcated fluid path including: a first flow path 34 for directing at least a first portion of the effluent back to the reservoir 36 or to a second chromatography through the opening of a first valve 30; and a second flow path 38 for directing at least a second portion of the effluent to an exit of the chromatography system through a second valve 32. First valve 30 and second valve 32, are each located downstream of column 24, and may be operably connected to a third and a fourth driver circuit, respectively, in the controller 40.

The sensor 28, for example, a UV sensor, is tied to a continuously variable speed load pump 22 in a feedback control loop, with an option to divert the effluent as a feed stream back to the load vessel or reservoir 36 by closing second valve 32 and opening first valve 30. Alternatively, the effluent can be directed to a second chromatography column (not shown in FIG. 1) with additional binding capacity by closing second valve 32 and opening first valve 30, allowing it to flow onto a second chromatography column. Rather than a dual speed load with speeds chosen arbitrarily, the chromatography system according to an embodiment of the invention allows a true feedback control across continuously variable load rates.

As the sensor 28 indicates the presence and/or a concentration of a material of interest in the post-separation stream, also referred to herein as the main downstream effluent path 26 extending from the outlet end of the chromatography column 24, the rate of pumping by the continuously variable speed pump 22 is slowed in order to increase binding by increasing residence time residence time and increase binding capacity. The sensor 28 and pump 22 operate in a feedback loop, for example, a Proportional-Integral-Derivative (PID) control to optimize loading in terms of both time and speed. The PID control utilizes a "hunting and seeking" technique to establish a control set-point relatively quickly, utilizing historical trending data.

In a method according to an embodiment of the invention, the sensor 28 and the variable speed pump 22 operate in a feedback loop to optimize a loading of the chromatography column 24 in terms of both time and speed.

In one example, second valve 32 would be closed and first valve 30 would be opened in order to route material back to the load vessel or reservoir 36 or to a second chromatography column (not shown) if the sensor 28 indicates that the amount of protein being lost in the post separation stream in the main downstream effluent path 26 exceeds a pre-determined level. For example, a relatively high UV absorbance indicates an undesirably high level of protein in the effluent in the effluent path 26.

On the other hand, if the sensor 28 indicates that the amount of protein being lost in the post separation stream or main downstream effluent path 26 is less than a pre-determined level, indicating that the desired material is being retained on the chromatography column 24, the first valve 30 would be closed and second valve 32 would be open in order to collect the effluent, or to allow the effluent to exit the chromatography system 20 by flowing out of the loop, for example to a waste container, or a product collection container.

This method of closing first valve 30 and opening second valve 32 could easily be combined with SMB/SMCC by diverting the feed stream to a third chromatography column if the effluent exceeds a pre-determined level of protein (e.g. high UV absorbance). Allowing the effluent to flow to a second column expands the system for further processing.

One embodiment of the invention is a system for variable speed feedback control chromatography loading comprising: a reservoir 36 for holding a fluid; a continuously variable speed pump 22 positioned for pumping the fluid from the reservoir 36 at a variable rate; a first chromatography column 24 positioned downstream of the pump 22 for receiving the fluid pumped from the reservoir 36, the chromatography column 24 having an upper end or inlet end for receiving the fluid, and a lower end or outlet end for allowing the effluent to flow out of the chromatography column 24; a main downstream effluent path 26 downstream of the outlet end of the first chromatography column 24; a sensor 28 positioned in the main downstream effluent path 26, the sensor 28 capable of detecting a signal indicative of a component or a concentration of the component in an effluent in the main downstream effluent path 26. A closeable bifurcated fluid path is communicatively coupled to the main downstream effluent path, the closeable bifurcated fluid path including: a first flow path 34 for directing at least a first portion of the effluent back to the reservoir 36 or to a second chromatography column; and a second flow path 38 for directing at least a second portion of the effluent to an exit of the chromatography system through an opening of valve 32. When first valve 30 is in an open position, effluent can flow back to the reservoir 36 or to a second chromatography column. When the second valve 32 is in an open position, effluent can flow to a waste container or to a product collection container. A controller 40 is operably connected to the continuously variable speed pump 22 in order to control the rate of pumping, and to each of the sensor 28, the first valve 30 and the second valve 32, such that the controller 40 signals the opening and/or closing of the first valve 30 and the second valve 32 in response to a signal from the sensor 28, the signal indicating the presence of the component or a pre-determined concentration of the component in the effluent.

Figure 2:
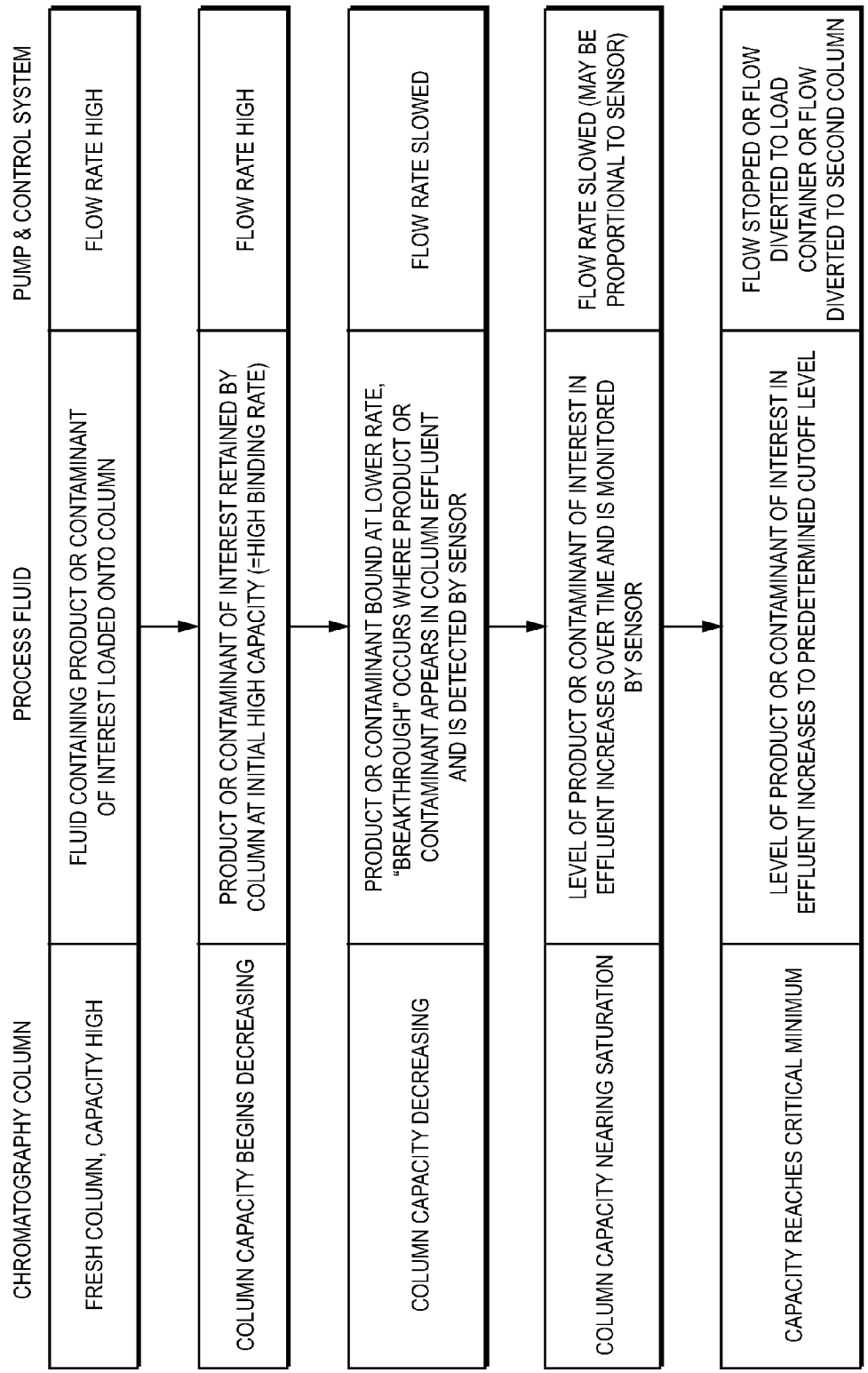
FIG. 2 is a chart showing a method of variable speed chromatography loading according to one embodiment of the invention.

FIG. 2 is a chart showing a method of variable speed chromatography loading according to one embodiment of the invention. The capacity of the chromatography column is described in the left hand column of the chart. The middle column describes the status of the process fluid. The right hand column shows the flow rate of the pump in response to the controller.

In a fresh column with high capacity, as shown in the first row, the fluid containing product or contaminant of interest is loaded onto the column. The flow rate is high.

As the column capacity begins decreasing, as shown in the second row, the product or contaminant of interest is retained by the column at initial high capacity. The binding rate is high and the flow rate is high.

The middle row of the chart shows column capacity decreasing. Therefore, the product or contaminant is bound at lower rate. "Breakthrough" occurs where product or contaminant appears in the column effluent and is detected by a sensor. The flow rate is slowed.

In the fourth row, the column capacity is nearing saturation. The level of product or contaminant of interest in the effluent increases over time, and is monitored by the sensor. The flow rate is slowed and maybe proportional to the sensor signal.

In the bottom row, the column capacity reaches a critical minimum. The level of product or contaminant of interest in the effluent increases to a predetermined cutoff level. The flow is stopped or the flow is diverted to a load container or flow is diverted to a second column (not shown).

Yet other embodiments of the invention comprise a control system wherein a given signal from sensor 28 can either slow the rate of pumping or increase the rate of pumping by pump 22, wherein such rates of pumping are infinitely variable.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A chromatography system for monitoring a process condition and in real time adjusting a chromatographic operating parameter to the process condition, the chromatography system comprising:
   a first chromatography column having an inlet end and an outlet end and adapted to contain a porous matrix;
   a pump having a continuously variable pumping speed and set to pump a fluid at a continuously variable rate from a reservoir into the inlet end of the chromatography column;
   a main downstream effluent path extending from the outlet end of the chromatography column, the main downstream effluent path for generally directing an effluent flowing out of the outlet end of the chromatography column;
   a closeable bifurcated fluid path communicatively coupled to the main downstream effluent path, the closeable bifurcated fluid path including:
   a first flow path for directing at least a first portion of the effluent back to the reservoir; and
   a second flow path for directing at least a second portion of the effluent to an exit of the chromatography system;
   a sensor positioned in the main downstream effluent path and configured to detect at least one signal indicative of the presence or absence of a component in the effluent, wherein the component is indicative of a process condition within the chromatography system;
   a controller operably connected to the sensor, and to the pump;
   a first valve operably connected to the controller and positioned in the first flow path such that when the first valve is in an open position, effluent can flow back to the reservoir; and
   a second valve operably connected to the controller and positioned in the second flow path, such that when the second valve is in an open position, effluent can exit the chromatography system, and wherein the position of the first valve and the position of the second valve are each operably controlled by the controller,
   wherein the operable connection of the controller to the sensor and to the pump is configured such that the controller can signal the opening and/or closing of the first valve and the second valve and/or the speed of the pump in response to the signal from the sensor, such that when the signal from the sensor indicates the presence of the component or a pre-determined concentration of the component in the effluent the controller signals the opening of the first valve and the closing the second valve.

2. The chromatography system of claim 1, wherein the sensor is capable of detecting a signal indicative of the concentration of the component.

3. The chromatography system of claim 1, wherein the second flow path for directing at least a second portion of the effluent to an exit of the chromatography system is configured such that, when the second valve is in the open position, the effluent exiting the chromatography system is directed to a second and a third chromatography column, a collection vessel, or a waste container.

4. The chromatography system of claim 3, wherein at least one of the first chromatography column, the second chromatography column, and the sensor is single use or disposable.

5. The chromatography system of claim 1, wherein the controller operably connected to the sensor and to the pump is configured to continuously increase the speed of the pump or to continuously decrease the speed of the pump in response to the at least one signal from the sensor.

* * * * *